United States Patent [19]

Carlson

[11] Patent Number: 4,983,530

[45] Date of Patent: Jan. 8, 1991

[54] SANDWICH IMMUNOASSAY FOR DETERMINATION OF TOTAL MONOCLONAL IGG

[75] Inventor: Charles W. Carlson, West Grove, Pa.

[73] Assignee: E. I. Du Pont de Nemours and Company, Wilmington, Del.

[21] Appl. No.: 150,292

[22] Filed: Jan. 29, 1988

[51] Int. Cl.$^5$ ................. G01N 33/543; G01N 33/577
[52] U.S. Cl. .................................... 436/518; 436/538; 436/548; 436/815
[58] Field of Search ..................... 435/7, 172.2, 240.26, 435/240.27, 68, 70.21; 436/518, 548, 513, 815, 824, 538; 530/387, 810, 827, 838

[56] References Cited

U.S. PATENT DOCUMENTS 4,486,530 12/1984 David et al. ................... 436/529 X
4,618,589 10/1986 Jefferis et al. ..................... 436/540

FOREIGN PATENT DOCUMENTS 243184  2/1987  Fed. Rep. of Germany .

OTHER PUBLICATIONS

Lowe et al., Immunology, vol. 42, 649 (1981), pp. 649–659.
Axiak et al., Journal of Immunological Methods, vol. 99, 141 (1987), pp. 141–147.
Springer, T. et al., Hybridoma 1 No. 3:257–273 (1982).

Primary Examiner—Esther L. Kepplinger
Assistant Examiner—David A. Saunders
Attorney, Agent, or Firm—Roseanne R. Duffy

[57] ABSTRACT

A sandwich immunoassay for determining total monoclonal IgG content in samples of purified IgG, cell culture medium and ascites fluid is provided based on the utilization of anti-light-chain IgG antibodies as both capture and label antibodies.

5 Claims, No Drawings

SANDWICH IMMUNOASSAY FOR DETERMINATION OF TOTAL MONOCLONAL IGG

TECHNICAL FIELD

This invention relates to the determination of total monoclonal IgG content in a sample of ascites fluid, cell culture medium or purified IgG by a sandwich immunoassay utilizing antibodies specific for IgG light chains.

The determination of total monoclonal IgG is important as a quality control tool for screening commercial antisera and for monitoring monoclonal cell lines for antibody production.

Traditional immunoassays for the determination of total monoclonal IgG use antisera containing both light and heavy chain antibodies. Barandun et al., Protides Biol. Fluids, Proc. Colloq., Volume 20, 573 (1972), describe a double line precipitation immunoassay which uses an antiserum containing a mixture of anti-kappa-light-chain IgG antibody and an anti-gamma-heavy-chain IgG antibody. A widely used immunoassay for the determination of total monoclonal IgG is a sandwich immunoassay which uses a polyclonal antiserum containinq both anti-light and anti-heavy-chain IgG antibodies both as the capture and label antibodies. The amount of monoclonal IgG is derived from the plot of a standard curve.

Even though the sandwich immunoassay is widely used it is impractical and has disadvantages. IgG heavy chains are divided into subclasses. The number of subclasses is dependent on the animal species. A monoclonal cell line produces only one subclass of IgG heavy chains which can vary from cell line to cell line. An antibody directed against one subclass can react with all other subclasses, but the extent of the reaction will not be the same for all subclasses. Polyclonal antiserum can be used to assay any sample containing monoclonal IgG regardless of what subclass is present since the antiserum contains approximately the same ratio of each subclass. However, each subclass will react differently to the polyclonal antiserum and responses will differ from sample to sample. Because of this difference in response, a different purified calibrator must be used to prepare a standard curve for every sample of monoclonal IgG assayed. Even though this assay works, it is impractical because of the need for a separate calibrator for every monoclonal cell line.

Another disadvantage of the traditional sandwich immunoassay is that it cannot be used to determine total monoclonal IgG in samples of ascites fluid. Ascites fluid contains approximately 5-30% nonspecific immunoglobulin, 70-95% of which is IgG, contributed by the host. The heavy chains of the host IgG are comprised of a mixture of subclasses which react differently to the polyclonal antiserum than do the heavy chains of the monoclonal IgG which are comprised of only one subclass. Each sample of ascites fluid contains a different mixture of heavy chain IgG subclasses. For this reason, no calibrator can be made available and determination of total monoclonal IgG or total IgG content cannot be accurately performed using the traditional sandwich immunoassay. Currently, HPLC is the only method available for determining total IgG content in samples of ascites fluid.

Monoclonal antibodies specific for the light chains of human immunoglobulins have been prepared and used in immunoassays for immunoglobulins and IgG subpopulations in human biological fluids. Lowe et al., Immunology. Vol. 42, 649 (1981) and DD 243184, published Feb. 25, 1987, describe the preparation of monoclonal antibodies to human immunoglobulin light chains and their use for the detection of B lymphocyte cell-surface immunoglobulins. The latter also describes the use of these monoclonal antibodies for quantitative and qualitative analysis of immunoglobulins in biological fluids.

Axiak et al., Journal of Immunological Methods, Vol. 99, 141 (1987), describe an inhibition enzyme-linked immunoassay which uses a monoclonal anti-kappa-light-chain IgG antibody to determine the presence of free kappa light chain immunoglobulin fragments in human urine and serum. First a sample is incubated with biotinylated monoclonal anti-kappa-light-chain IgG antibody, then an aliquot of the mixture is incubated with immobilized kappa chains and the amount of biotinylated antibody bound to the immobilized kappa chains is measured. The monoclonal antibody of this assay is specific for free kappa chain only. According to the authors, the anti-kappa-light-chain IgG antibody will not react with heavy-chain associated kappa light chains since the binding site recognized by the antibody will not be expressed when the kappa chain is attached to the heavy chain and, for this reason cannot be used in an immunoassay for total IgG.

U.S. Pat. No. 4,618,589, issued Oct. 21, 1986, to Jefferis et al., discloses an immunoprecipitation assay using monoclonal antibodies specific to two distinct antigenic binding sites on the IgG molecule to determine either total IgG or a sub-population of IgG in a human sample. This assay requires two monoclonal antibodies specific to different binding sites in order to form a measurable precipitate. The use of only monoclonal anti-light-chain IgG antibodies will not yield such precipitates.

There is a need for a practical immunoassay for the determination of total monoclonal IgG content which can be performed on cell culture medium, ascites fluid, and purified IgG and requires only a single calibrator.

DISCLOSURE OF THE INVENTION

The sandwich immunoassay of this invention for the determination of total monoclonal IgG content comprises the steps of:

(a) forming a first reaction mixture by contacting a sample containing monoclonal IgG with a support bearing
  (i) both anti-kappa and anti-lambda-light-chain IgG capture antibodies specific for said monoclonal IgG or
  (ii) an IgG capture antibody specific for the predominant IgG light chain type in the animal species from which the monoclonal IgG originated, provided that said IgG light chain type comprises at least 95% of the total IgG in said animal species;

(b) separating a bound first complex of capture antibody and monoclonal IgG formed in step (a) from unbound monoclonal IgG:

(c) forming a second reaction mixture by contacting said first complex with at least one labeled anti-light-chain IgG antibody having the same specificity for IgG light chain type as the capture antibody;

(d) separating the bound second complex of labeled antibody and said first complex so formed from unbound labeled antibody;

(e) determining the amount of label in the second complex; and (f) calculating the total monoclonal IgG content from a standard curve prepared by using a calibrator.

DESCRIPTION OF THE INVENTION

The sandwich immunoassay of this invention is useful for determining total monoclonal IgG content in samples of monoclonal IgG in a convenient manner. These samples include cell culture medium ascites fluid and purified IgG.

An important aspect of this invention is the use of antibodies specific for IgG light chains. Since there are only two subclasses of IgG light chain, kappa and lambda, the response to the anti-light-chain IgG antibodies by the monoclonal IgG in the sample will be similar for each sample of monoclonal IgG assayed.

In samples of ascites fluid, however, host-contributed IgG will also be measured since the anti-light-chain IgG antibodies of this invention do not distinguish between monoclonal IgG and adventitious IgG. So, in effect, for samples such as ascites fluid which contain host-contributed IgG, total IgG content, i.e. monoclonal IgG and host-contributed IgG will be measured. In general, since host-contributed IgG amounts to less than 30% of the total IgG, and can be as little as approximately 3%, in an ascites fluid sample, the measurement of IgG contributed by the host will usually be within the accuracy level of the assays employed. Host-contributed non-IgG immunoglobulin might also be detected but the amount will be insignificant.

The anti-kappa and anti-lambda-light-chain IgG antibodies can be obtained by known methods. For example, tree kappa light chain IgG fragments can be isolated from the urine of tumor-bearing mice and inoculated into an immunocompetent host, such as a rabbit causing the production of circulating antibodies specific for mouse kappa light chain IgG. Since capture antibodies must be specific for monoclonal IgG contained in a sample, the immunogen must be of the same animal species as that from which the monoclonal IgG originated. The serum can be harvested and used directly provided an appropriate activity level has been reached or antibodies can be isolated and purified from the serum by known methods. Purified antibodies can be used whole, or can be fragmented by enzyme digestion using e.g. papain or pepsin to produce monovalent or divalent antibody fragments, respectively. Whole antibody purified from immune serum is preferred. Alternatively lymphocytes can be obtained from the host animal and when these lymphocytes are fused with appropriate immortal cells, such as myeloma cells they will produce hybridoma cells capable of secreting desired monoclonal antibodies. These techniques are familiar to those skilled in the art; a general description can be found in Mayer et al. Immunochemical Methods in the Biological Sciences: Enzymes and Proteins Academic Press, London, 1980, pages 5-17.

The capture antibodies of this invention are immobilized on a support and bind the monoclonal IgG, removing it from the sample. The capture antibodies can be immobilized on any of the common supports used in immunometric assays. The supports can be solid or liquid and include polystyrenes, polyethylenes, polycarbonates, perfluorocarbon polymers, glass, coated magnetic particles and a variety of latex particles. A polystyrene microtiter plate is the support of choice.

Labeled anti-light-chain IgG antibodies can be readily obtained commercially or prepared by general conjugation techniques. Any detectable label can be utilized in the immunoassay of this invention. These include radioisotopes, luminescent materials, fluorophores, and enzymes. Enzymes are preferred.

The sandwich immunoassay of the present invention is a heterogeneous sandwich immunoassay performed by contacting immobilized anti-light-chain IgG antibodies with the sample containing monoclonal IgG to form a first complex and then contacting this complex with labeled anti-light-chain IgG antibodies.

Specifically, a first reaction mixture is formed by contacting the sample containing monoclonal IgG with a support bearing at least one of anti-kappa and anti-lambda-light-chain IgG capture antibodies and incubating the reaction mixture for a time and at a temperature sufficient to permit the substantially complete formation of an immune complex, usually approximately for one hour at 37° C. Antibodies specific for a single IgG light chain type can be used where that light chain type comprises at least 95% of the total IgG in the animal species from which the monoclonal IgG originated. The distribution of IgG kappa and lambda light chains differs from species to species. Since a sample containing monoclonal IgG is comprised of only one IgG light chain type, the probability of that IgG light chain type being kappa or lambda is dependent on the animal species from which the monoclonal IgG originated. For example, mouse IgG is approximately 95% kappa light chain and horse IgG is substantially 100% lambda light chain. Therefore, an approximately 95% probability exists that a sample containing mouse monoclonal IgG will be comprised of kappa light chain only and a 100% probability exists that a sample containing horse monoclonal IgG will be comprised of lambda light chain. (Atassi et al., Molecular Immunology: A Textbook, Marcel Dekker, Inc., New York, 1984, page 155). For those samples containing monoclonal IgG which originated from species in which no IgG light chain type is predominant, such as human IgG, both anti-kappa and anti-lambda-light-chain IgG antibodies must be used to assure that the monoclonal IgG present in the sample will be captured and measured regardless of which IgG light chain type is present.

The bound monoclonal IgG in the first complex can be separated from unbound monoclonal IgG by any convenient means such as filtration and centrifugation. The support bearing the first complex of capture antibody and monoclonal IgG is then contacted with labeled anti-light-chain IgG antibodies. The formation of a second immune complex is again allowed to go to substantial completion approximately for one hour at room temperature. This second complex of labeled anti-light-chain IgG antibody and first complex is then separated from the unbound labeled antibody.

The labeled antibodies can be specific for a single IgG light chain type or for both IgG light chains, depending on the specificity for light chain type of the capture antibodies or the nature of the predominant light chain type in the animal species from which the sample of monoclonal IgG was obtained. Where the capture antibody is specific for a single IgG light chain type, the labeled antibodies can be specific for both IgG light chains or for the same single IgG light chain type. Since capture antibody specific for a single IgG light chain type is used only where a single IgG light chain type makes up at least 95% of the total IgG in an animal species from which a sample containing monoclonal IgG is obtained, the use of labeled anti-light-chain IgG antibodies specific for both IgG light chains will have little effect on the determination of total monoclonal IgG content. Where the capture antibodies are specific for both IgG light chains, the labeled anti-light-chain IgG antibodies can be specific for both IgG light chains or for one IgG light chain type. For example, in an assay for the determination of total monoclonal IgG in a sample containinq mouse monoclonal IgG, if the capture antibody is only anti-kappa-light-chain IgG antibody, then the labeled anti-light-chain IgG antibodies can be anti-kappa-light-chain IgG antibody or a mixture of anti-kappa and anti-lambda-light-chain IgG antibodies. If the capture antibodies are both anti-kappa and anti-lambda-light-chain IgG antibodies, then the labeled anti-light-chain IgG antibodies can be a mixture of anti-kappa and anti-lambda-light-chain IgG antibodies or, preferably, anti-kappa-light-chain IgG antibody.

The amount of label in the second complex which is a measure of the total monoclonal IgG content of the sample, is then determined: the method of determination depending on the label used. For example, where the label is a radioisotope the measurement is conducted using radioactivity counting equipment. Where the label is a fluorophore, the measurement is conducted using a fluorospectrophotometer. The nature of the label can require the addition of an appropriate substrate before the label can be measured. For example, the label can be an enzyme which directly converts a substrate to a colored end-product.

Total monoclonal IgG can be calculated from a plot of a standard curve prepared through the use of a calibrator. The calibrators of this invention are unique in that only a single calibrator is necessary for assaying simultaneously several samples of the same type containing monoclonal IgG from different monoclonal cell lines of the same species. Also, for the first time a calibrator is available for assaying ascites fluid. The calibrator used is dependent on the type of sample being assayed. Where the sample containing monoclonal IgG is cell culture medium, the calibrator is pooled freeze-dried IgG rehydrated with either fresh culture medium which is the same as the culture medium in the sample or PBS. Rehydratinq with fresh culture medium is preferred. Where the sample containing monoclonal IgG is ascites fluid, the calibrator is pooled freeze-dried IgG rehydrated with ascites fluid which has been stripped of all IgG. IgG can be removed by passing the ascites fluid through a Protein A chromatographic column.

The sandwich immunoassay of this invention has several advantages over the traditional assays for determining total monoclonal IgG content. Since the assay uses anti-light-chain IgG antibodies, there is no difference in response due to heavy chain subclasses. Responses are similar from monoclonal cell line to monoclonal cell line and only one calibrator is necessary. For the same reason the assay can also be used to determine total monoclonal IgG in samples of ascites fluids. Variable responses due to heavy chain subclasses of host-contributed IgG do not interfere with the assay. In addition, a single calibrator has been found to work with any sample of ascites fluid. Determination of total monoclonal IgG content in ascites fluid is especially important for monitoring cell lines grown in vivo for antibody production.

The following example illustrates the invention:

EXAMPLE

Determination of Total IgG Content in Ascites Fluid Samples

A flat-bottomed 96-well microtiter plate (Immulon 2, available from Titertek) was first washed with deionized water and blotted dry. The capture antibody, sheep anti-mouse-kappa-light-chain IgG antiserum [available from Nordic, catalog number ShAM/BJ-K(SD+HD)/7S], was diluted 1:200 in 0.1 M bicarbonate buffer (pH 9 5) and 100 μL of antibody solution was added to each well. The plate was covered and incubated at 37° C. for 2 hr and then stored at 4° C. overnight. The plate was then washed thoroughly with a wash buffer (0.15 M sodium chloride, 0.01 M sodium dihydrogen phosphate, 0.1% 2-chloroacetamide, 0.5% Triton X-100; pH 7.8) to remove any unbound capture antibody and blotted dry. 200 μL of blocking buffer (0.1 M sodium bicarbonate, 0.05 % Triton X-100, 2.0% by volume horse serum: pH 9.5) was added to each well, the plate was incubated for 1 hr at room temperature, and then thoroughly washed with the wash buffer.

Calibrators were prepared by rehydrating pooled freeze-dried affinity-purified mouse IgG (available from Zymed, catalog number 02-6502) with mouse ascites fluid stripped of IgG to give a 5 mg IgG/mL solution. The calibrator was diluted with diluting buffer (0.5 M sodium chloride, 0.01 M sodium dihydrogen phosphate 0.05% Triton X-100, 2.0% by volume horse serum: pH 7.8) to prepare the final dilutions shown in Table 1.

TABLE 1

| CALIBRATOR DILUTION | IgG CONCENTRATION OF CALIBRATOR (μg/mL) |
| --- | --- |
| 1:100 | 50 |
| 1:200 | 25 |
| 1:400 | 12.5 |
| 1:800 | 6.25 |
| 1:1600 | 3.125 |
| 1:3200 | 1.563 |
| 1:6400 | 0.781 |
| 1:12800 | 0.391 |

Three samples each of monoclonal ascites fluid samples containinq antibodies to human chorionic gonadotropin (HCG), carcinoembryonicantigen (CEA) and phenytoin (PTN) were diluted in the same manner as the calibrator. 50-μL aliquots of calibrator and sample dilutions were added to each well of the plate. The plate was incubated at 37° C. for 1 hr then washed thoroughly with wash buffer.

A labeled anti-light-chain IgG antibody, rabbit anti-mouse-kappa-light-chain IgG Horse Radish Peroxidase Conjugate [available from Nordic, catalog number ShAM/BJ-L(SD+HD/PO], was diluted 1:200 with diluting buffer and 100 μL added to each well. The plate was incubated at room temperature for 1 hr and then washed thoroughly with wash buffer.

Peroxidase Substrates A and B (available from Kirkegaard and Perry, catalog number 50-64-00) were mixed 1:1 and 100 μL of this mixture was added to each well. The plate was placed on a plate shaker and the absorbance of each well was read at 410 nM using a Titertek Multiskan MCC Plate Reader after a substrate reaction period of 20 minutes.

The average value total IgG content of the ascites fluid samples containing monoclonal antibodies to CEA, HCG and PTN was calculated and compared to the total IgG content determined by HPLC. The data presented in Table 2 show good correlation between the total IgG content determined by the sandwich immunoassay of this invention and that determined by HPLC.

TABLE 2

| MONOCLONAL ANTIBODY TO | SANDWICH IMMUNOASSAY (mg/mL) | HPLC (mg/mL) |
| --- | --- | --- |
| HCG | 6.6 | 6.2 |
| CEA | 2.5 | 2.3 |
| PTN | 6.6 | 4.9 |

What is claimed:

1. A sandwich immunoassay for the determination of total monoclonal IgG content comprising the steps of:
   (a) forming a first reaction mixture by contacting a sample containing monoclonal IgG with a support bearing
      (i) both anti-kappa and anti-lambda-light-chain IgG capture antibodies specific for said monoclonal IgG or
      (ii) an IgG capture antibody specific for the predominant IgG light chain type in the animal species from which the monoclonal IgG originated, provided that said IgG light chain type comprises at least 95% of the total IgG in said animal species;
   (b) separating a bound first complex of capture antibody and monoclonal IgG formed in step (a) from unbound monoclonal IgG:
   (c) forming a second reaction mixture by contacting said first complex with at least one labeled anti-light-chain IgG antibody having the same specificity for IgG light chain type as the capture antibody;
   (d) separating the bound second complex of labeled antibody and said first complex so formed from the unbound labeled antibody;
   (e) determining the amount of label in the second complex; and
   (f) calculating the total monoclonal IgG content from a standard curve prepared by using a calibrator.

2. The sandwich immunoassay of claim 1 for monoclonal IgG in culture medium wherein the calibrator is pooled freeze-dried IgG rehydrated with fresh culture medium or PBS.

3. The sandwich immunoassay of claim 1 for monoclonal IgG in ascites fluid wherein the calibrator is pooled freeze-dried IgG rehydrated with IgG-free ascites fluid.

4. The sandwich immunoassay of claim 1 wherein the labeled anti-light-chain IgG antibody is specific for the predominant IgG light chain type in the animal species from which the sample of monoclonal IgG originated, provided that said IgG light chain type comprises at least 95% of the total IgG in said animal species.

5. The sandwich immunoassay of claim 1 wherein the support is solid.

* * * * *